United States Patent [19]

Wilis

[11] Patent Number: 5,223,783

[45] Date of Patent: Jun. 29, 1993

[54] METHOD AND DEVICE FOR DETECTING REDUCING GAS USING SEMICONDUCTOR GAS SENSOR

[75] Inventor: Alexander N. Wilis, Hollister, Calif.

[73] Assignee: Willis Technologies International, Inc., Falls Church, Va.

[21] Appl. No.: 877,500

[22] Filed: May 1, 1992

[51] Int. Cl.[5] .................................. G01N 27/00
[52] U.S. Cl. ................................ 324/71.5; 73/1 G;
        73/23.2; 204/409; 422/98; 422/110; 436/127
[58] Field of Search ............... 324/71.5, 693; 204/409;
        422/92, 98, 107, 110, 111; 436/127; 73/1 G,
        23.2, 23.36, 31.01

[56] References Cited

U.S. PATENT DOCUMENTS

| | | | |
|---|---|---|---|
| 2,965,842 | 12/1960 | Jacobson | 324/701 |
| 3,039,053 | 6/1962 | Jacobson | 324/71.1 |
| 3,479,257 | 11/1969 | Shaver | 204/153.13 X |
| 3,678,513 | 7/1972 | Ward, Jr. | 340/519 |
| 3,815,114 | 6/1974 | Johnson et al. | 422/95 |
| 3,924,442 | 12/1975 | Kerho et al. | 73/1 G X |
| 4,030,340 | 6/1977 | Chang | 422/98 X |
| 4,197,089 | 4/1980 | Willis et al. | 324/71.5 X |
| 4,384,925 | 5/1983 | Stetter et al. | 204/409 X |
| 4,387,165 | 6/1983 | Youngblood | 436/121 |
| 4,590,789 | 5/1986 | Kunze | 73/1 G |
| 4,691,167 | 9/1987 | Vlekkert et al. | 324/71.5 X |
| 4,758,408 | 7/1988 | Krawetz et al. | 422/92 |
| 4,822,465 | 4/1989 | Jones et al. | 204/192.1 |
| 4,825,683 | 5/1989 | Takami et al. | 73/1 G |

Primary Examiner—Jack B. Harvey
Assistant Examiner—Glenn W. Brown
Attorney, Agent, or Firm—Pennie & Edmonds

[57] ABSTRACT

A method and a device which uses a semiconductor type of sensor for detecting and measuring gas of the type such as hydrogen sulfide which depletes the oxygen component from the semiconductor sensor when exposed to the gas and thus lowers electrical resistance through the sensor which uses a pair of semiconductor gas detecting sensors. In one embodiment, the gas sensors are alternatively fed with gas to be sampled and air. In another embodiment, the gas sensors are alternatively turned on and off at predetermined intervals to replenish the depleted oxygen when the sensor is turned off and to sample when the sensor is turned on.

22 Claims, 6 Drawing Sheets

METHOD AND DEVICE FOR DETECTING REDUCING GAS USING SEMICONDUCTOR GAS SENSOR

BACKGROUND OF THE INVENTION

1. Field of the Invention

This invention relates to a method and a device for detecting and measuring the content of reducing gas, such as hydrogen sulfide, using a semiconductor type of sensors. Reducing gas depletes oxygen from the semiconductor sensors upon exposure thereto and lowers electrical resistance through the semiconductor component thereof.

2. Description of the Prior art

It is known to use semiconductor sensors for measuring gas, in particular for measuring hydrogen sulfide ($H_2S$) content existing in natural gas. U.S. Pat. Nos. 4,822,465 to Jones, et al.; 4,387,165 to Youngblood; 4,197,089 to Willis, et al.; 4,030,340 to Chang; 3,479,257 to Shaver; and the article entitled, "Electrochemical or Solid State $H_2S$ Sensors: Which is Right for You?" by Cheryl L. Kaminski and Albert Poli, InTech June 1985, for instance, disclose sensors for detecting a particular type of gas such as $H_2S$. In addition, U.S. Pat. No. 4,590,789 discloses a device for calibrating a gas sensor.

Generally, the principle of operation of a semiconductor sensor is as follows:

Gases capable of depleting $O_2$ from metal oxide semiconductor material is referred to as reducing gases. Metal oxide semiconductors absorb oxygen when exposed to air or gas containing oxygen and become oxidized at the surface thereof. The oxygen absorbed at the surface of the semiconductor generates an electrical field which repels the electrons from the surface.

A metal oxide semiconductor sensor is formed on a non-conducting substrate between two electrodes. Heating elements are also formed on the substrate to heat the semiconductor at a desired temperature. When the semiconductor is heated to certain temperature ranges, the reducing gas being monitored changes the conductivity of the metal oxide semiconductor. For example, upon exposure of the heated metal oxide semiconductor to reducing gas, such as $H_2S$, a measurable decrease in electrical resistance occurs through the metal oxide semiconductor. This change is believed to be caused by a combination of adsorption, oxidation/reduction, and anion exchange phenomena in the semiconductor material. Theoretically, under zero gas conditions (no exposure to gas being measured), $O_2$ molecules which are adsorbed/oxidized to the surface of the semiconductor, tie up free electrons in the semiconductor, thereby inhibiting electrical flow (high resistance). Reducing gas such as $H_2S$ replaces $O_2$, releasing the free electrons and thus decreasing the resistance between the electrodes. The decrease in electrical resistance is related to the concentration of the gas component being detected and sampled. The surface of the metal oxide semiconductor behaves much like a "biomass", breathing in oxygen and oxidizing the surface thereof, and exhaling oxygen, for example, in the form of $SO_2$ and $H_2O$ in the presence of $H_2S$.

Over a period of time, $O_2$ depletion will occur when the metal oxide semiconductor is exposed to gas such as $H_2S$. For proper operation, the presence of $O_2$ is required and the sensor thus must be replenished with $O_2$.

However, metal oxides semiconductors when exposed to air for prolonged periods without the presence of reducing gas such as $H_2S$ tend to continuously oxidize and cause their electrical resistance to increase greatly. This phenomena is generally know as "going to sleep". This does not mean that the sensors will no longer be operative, rather their span of operation moves into a much higher electrical resistance range, most likely into the range beyond the measuring capability of their associated electronic hardware. If the metal oxide sensors are exposed to air or have been greatly oxidized, they need to be exposed to reducing gas for a relatively long period to remove some of the oxidation before reading from the sensor can take place, substantially increasing the response time for reading.

In order to replenish $O_2$, the sensor must be exposed with ambient air or gas having oxygen for a predetermined time for the sensor to absorb $O_2$ lost during sampling. During this oxidation period, in the prior systems, sampling of gas cannot be contemplated.

U.S. Pat. Nos. 3,924,442 to Kerho, et al.; 3,815,114 to Johnson, et al.; 3,678,513 to Ward, Jr.; and 3,039,053 and 2,965,842 both to Jacobson disclose a system for detecting gas using a plurality of sensors. However, none of these patents disclose the device and the method contemplated in the present invention.

SUMMARY OF THE INVENTION

An object of the invention is to rhythmically cycle gas/air at optimum intervals to maintain a consistent output from the sensors and to maintain a reading response speed at an optimal consistent level.

Another object of the present invention is to continuously sample gas using a pair of sensors. By using a pair of sensors, continuous sampling can be made by alternatively sampling from one sensor while the other sensor is being replenished with $O_2$.

Another object of the invention is to provide a pair of sensors in a pair of a sampling chambers and alternatively sampling from one chamber at a time while replenishing the depleted oxygen in the sensor in the other chamber.

Another object of the invention is to provide at least a pair of sensors in a single chamber and alternatively turning on one sensor for sampling and turning off the other sensor for replenishing the depleted oxygen.

In the present invention, in one embodiment, a pair of gas chambers, each having a semiconductor gas detecting sensor is contemplated, rather than a single gas chamber with a gas detecting sensor. The gas to be sampled is fed through only one of the two chambers during sampling. In particular, the gas to be sampled is fed through the one chamber, while the other of the two chambers is fed with ambient air to purge any residue gas and to replenish the sensor with $O_2$. After a predetermined period, the one chamber that was sampling with gas is instead fed with ambient air to purge the gas and to replenish the sensor with $O_2$ depleted from exposure to reducing gas, while the other chamber that was being purged with ambient air is fed with the gas to be sampled. Then after the predetermined period, the role between the two chambers is switched again and repeated.

To carry out the above described method, in addition to the pair of chambers with the gas detecting sensors, a microprocessor is utilized to control the logistics of the operation. In particular, the present device contemplates using conventional semiconductor sensors of the type which lowers resistance across the semiconductor upon exposure to reducing gas which depletes $O_2$ from the semiconductor.

The output of each sensor is operatively connected to the microprocessor which displays the content of the oxygen depleting gas contained in the gas sampled, for example, $H_2S$ contained in natural gas. A pair of solenoid valves, each having an output is connected to the pair of chambers. Each solenoid valve has a pair of inputs respectively connected to a gas intake and an ambient air intake. Each solenoid valve is connected to and controlled by the microprocessor. By controlling the solenoid valves, each chamber can be connected to either the gas intake or the ambient air intake, but not both at the same time.

In another embodiment, a gas monitor for monitoring ambient environment, such as air, for hazardous gas, such as $H_2S$, contemplates use of at least a pair of metal oxide sensors. In this embodiment, no plumbing of any kind is required and thus individual "stand alone" single point systems can be contemplated. By simply having at least two metal oxide sensors housed in a single housing and switching each of the sensors "on" and "off" alternatively after a predetermined interval, similar effect as that of the first embodiment can be contemplated. By shutting off the sensor (turning off the heating element in the sensor), the temperature of the metal oxide semiconductor will cool to about the room temperature. This causes the metal oxide semiconductor to replenish the depleted oxygen even though a reducing gas can be present.

DESCRIPTION OF THE PREFERRED EMBODIMENT

Figure 1:
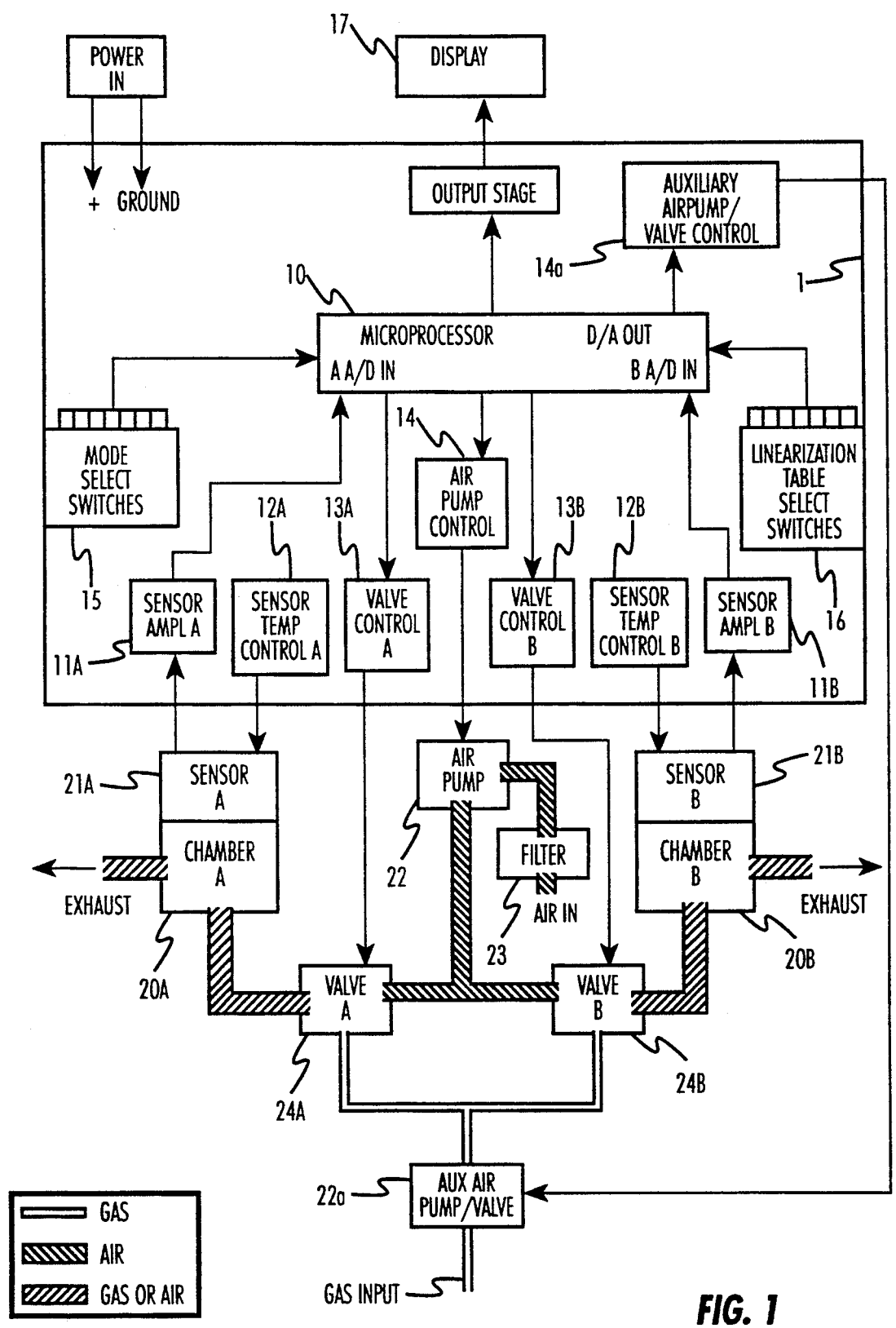
FIG. 1 is a block diagram of the electrical and mechanical components of the first embodiment of the present invention.

The present invention, as shown in the drawings contemplates at least two different embodiments. Same reference numerals have been designated to each embodiments for identifying the same elements.

FIG. 1 shows overall electrical and mechanical components of the present invention. The electrical control is housed inside a housing (1) to protect the same from the elements. The electrical control comprises a microprocessor (10), a sensor amplifier A (11A), a sensor amplifier B (11B), a sensor temperature control A (12A), a sensor temperature control circuitry B (12B), a valve control A (13A), a valve control B (13B), an air pump control (14), an auxiliary air pump or solenoid valve control (14a), mode select switches (15), linerization table select switches (16) and a meter (17) that shows the content of the oxygen depleting gas.

Figure 2:
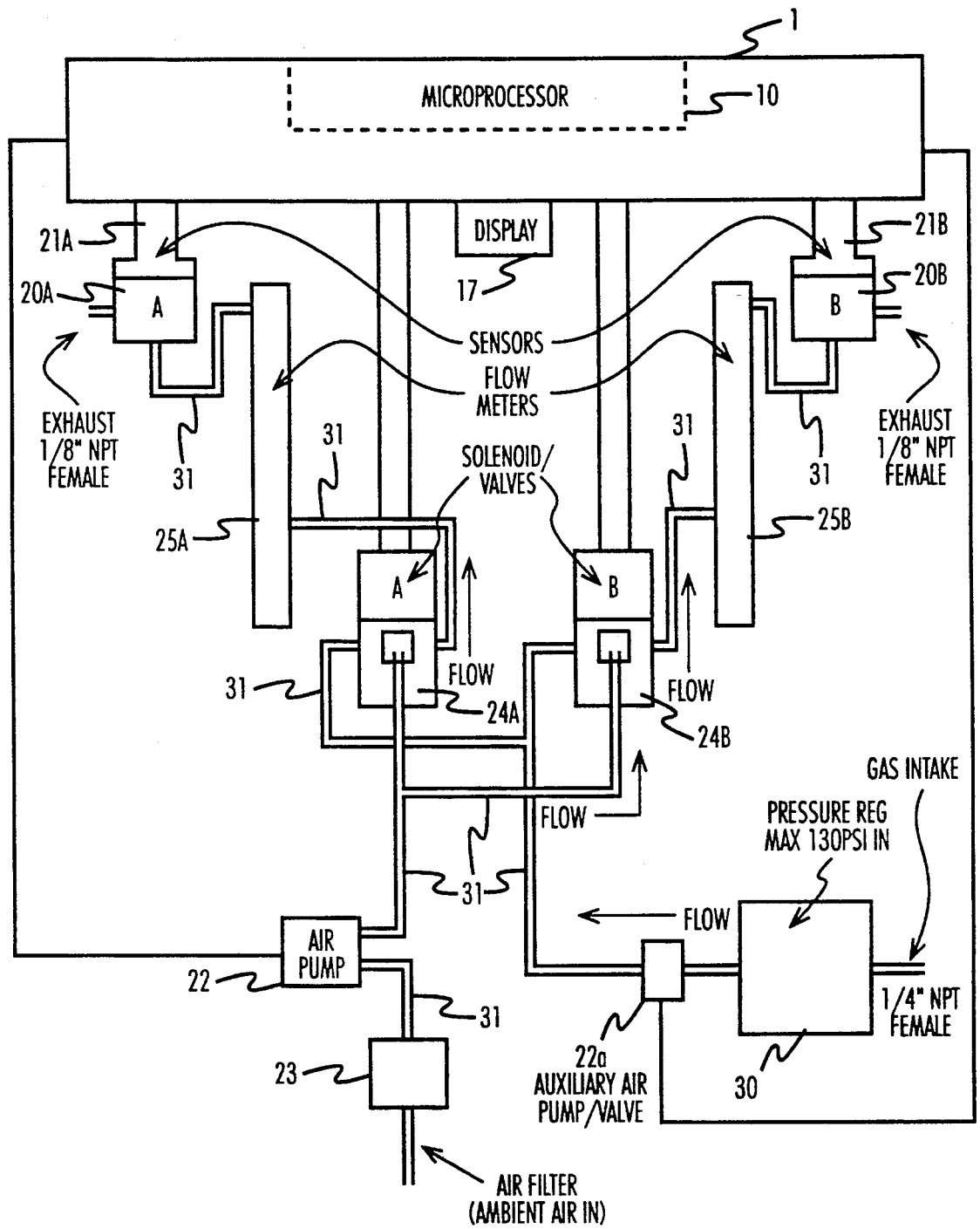
FIG. 2 is a physical connection of the electrical and mechanical components of the first embodiment of the present invention.
Figure 3:
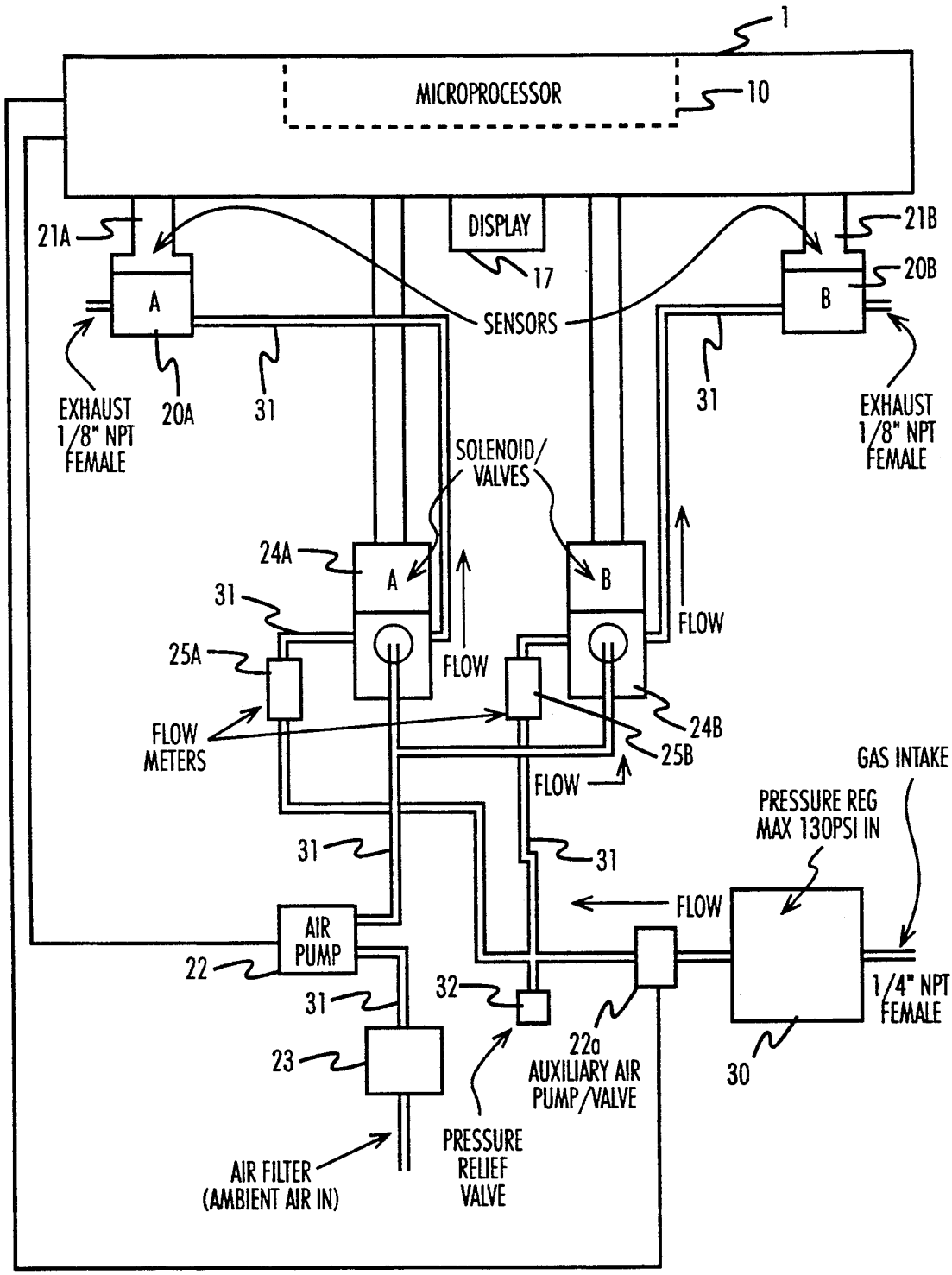
FIG. 3 is a slight variation of the electrical and mechanical components of FIG. 2.

The electro/mechanical components comprise a chamber A (20A) containing a sensor A (21A), a chamber B (20B) containing a sensor B (21B), an air pump (22), an auxiliary airpump or solenoid valve (22a), a filter (23) and a solenoid valve A (24A), a solenoid valve (24B) and a pair of flowmeters (25A, 25B), as shown in FIGS. 2 and 3.

As shown in better details in FIGS. 2 and 3, a pressure regulator (30) is used to regulate the pressure, maximum to 130 psi and gas lines capable of supplying at least 1.2 liters per minute of flow are used. Each of the gas chambers (20A, 20B) has a gas detector (21A, 21B) exposed to the flow of gas to be sampled, which lowers the electrical resistance across the detector in proportion to the amount of a certain gas component detected in the sampled gas such as $H_2S$ component existing in natural gas. The outputs of the sensors are connected to the sensor amplifiers (11A) and (11B) which boosts the signal to a level suitable for inputting to the microprocessor (10).

Each of the temperature controls (12A, 12B) is designed to control the heating elements contained in the respective sensors (21A, 21B) to a constant optimum operating temperature, independent of the ambient variations, optimized for a particular reducing gas being sampled.

Figure 5:
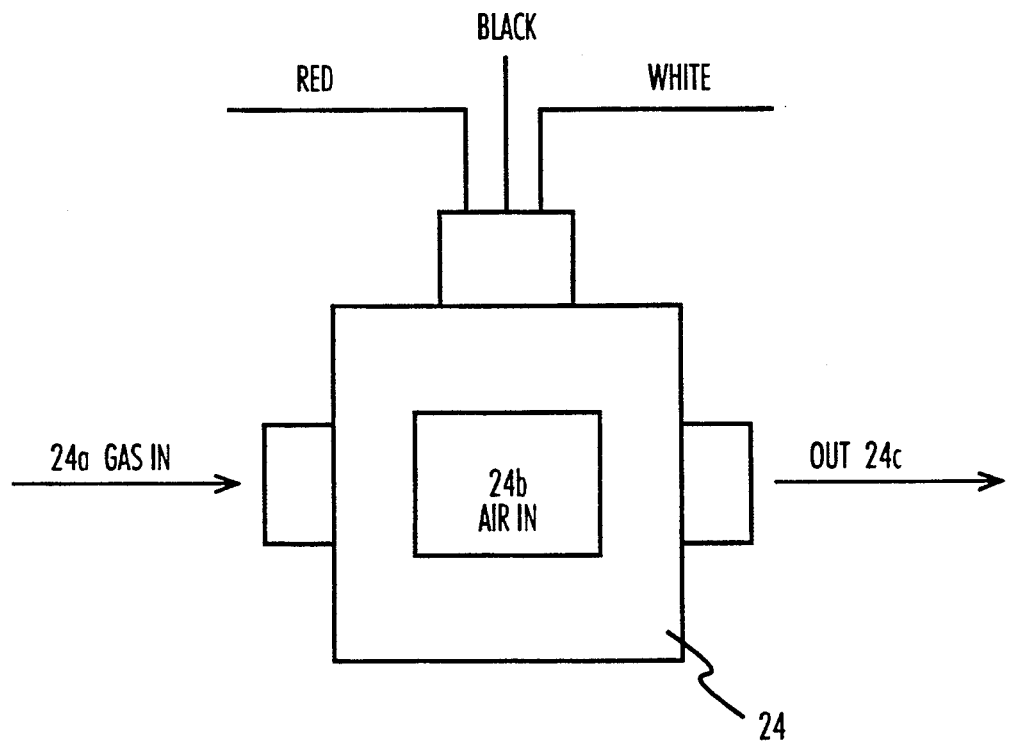
FIG. 5 is a graphical view of the solenoid operation.

In FIG. 2, the chambers (20A, 20B) are connected to the respective solenoid valves (24A, 24B) via gas line (31). Interposed between the solenoid valve (24A) and the chamber (20A) is a flowmeter (25A) for measuring the flow rate of the gas through the chamber (20A). Likewise, another flowmeter (25B) is interposed between the chamber (20B) and the solenoid valve (24B) for measuring the flow rate of the gas flowing through the chamber (20B). Each of the solenoid valves has a pair of inputs (24a, 24b) and a single outlet (24c), as shown in FIG. 5. One input (24b) is accommodated for ambient air and the other input (24a) is accommodated for gas.

The solenoid valves (24A, 24B) are connected to the ambient air and the gas via the gas pipes (31). However, by providing a pulse to either the red line or the black line, each solenoid valve can either enable the gas input or the air input to communicate to the output, but not both. The white line shown is a ground and the like. The solenoid remains where last pulsed, even with a power failure. Accordingly, the power consumption to operate the solenoid between pulses is zero.

In the embodiment of FIG. 2, since both flowmeters are placed downstream of their respective solenoid valve, each flowmeter can read flow of gas as well as the flow of air. In the embodiment of FIG. 3, the flowmeters (25A) are placed between the gas intake and the solenoid valve (24A). Likewise, the other flowmeter (25B) is placed between the gas intake and the respective solenoid valve (24B). Since both flowmeters are placed upstream of their respective solenoid valve for the gas line, each flowmeter can only read the flow of gas. The flowmeters, however, can be placed anywhere convenient. For example, use of only a single flowmeter can be contemplated by placing it in the gas intake, just downstream or upstream of the pressure regulator. Alternatively, one flowmeter can be placed just upstream of one solenoid valve and another flowmeter just downstream of the other solenoid valve.

In the embodiment of FIG. 3, if there is a defect in the solenoid valve which permits gas flow, through leakage, into the gas chamber when only air should be flowing, since the flowmeter is placed upstream of the solenoid valve for the gas line, the leakage can be detected.

An auxiliary air pump or solenoid valve (22a) is provided between the pressure regulator (30) and the solenoid valves (24A, 24B) in FIG. 2 and between the pressure regulator (30) and the pressure relief valve (32) in FIG. 3. The pump/valve (22a) is controlled by the microprocessor via the auxiliary control (14a) to turn on and off or to open and close either the air pump or solenoid valve (22a). By either turning on an air pump or opening a solenoid valve, air can be injected into the gas stream in small quantities. When the solenoid valve is used, air can be introduced into the gas stream by the venturi effect. That is, by merely creating a small opening about perpendicular to the flow of the gas and exposing the opening to ambient air, air will be sucked into the gas flow. An auxiliary air pump or a solenoid valve is used when the concentration of the reducing gas is relatively high so as to deplete $O_2$ from the sensor rapidly. By injecting air into the gas stream, oxygen depletion can be retarded. The solenoid valve (22a) can be of the type previously described, but requiring only one input for introducing ambient air.

Figure 4:
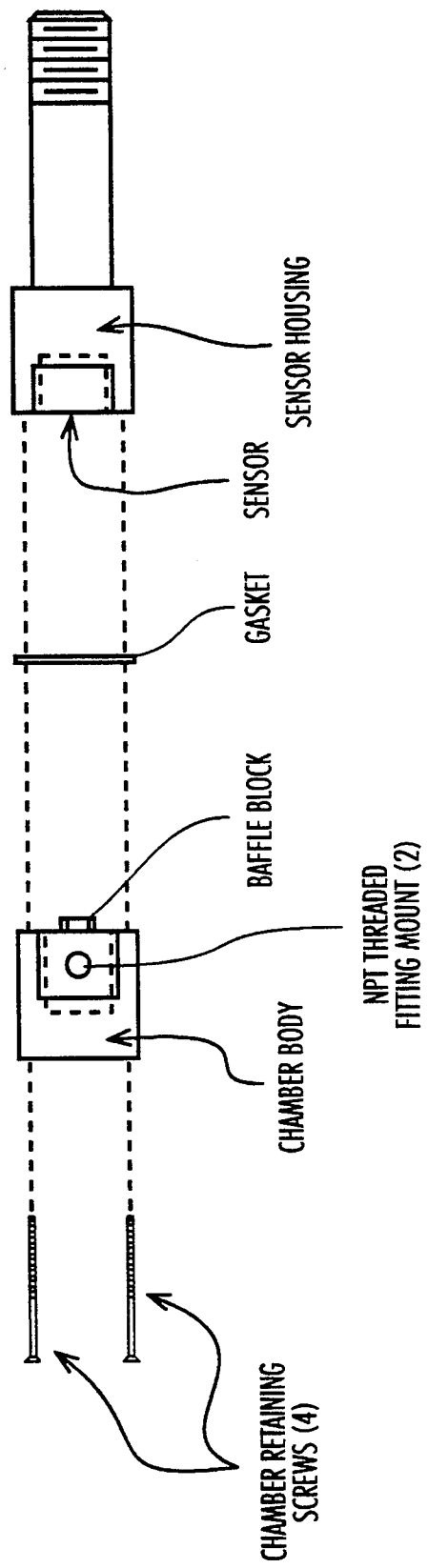
FIG. 4 is a detailed view of the sensor housing and chamber for the first embodiment.

FIG. 4 shows a chamber for housing a metal oxide semiconductor sensor in the first embodiment. In particular, chamber comprises the chamber body, gasket and the sensor housing which are all held together by a plurality of screws in the manner shown. It should be noted that the sensor need not be arranged in any particular manner as long as the sensor is exposed to the gas being sampled through the inlet end (NPT threaded fitting mount), except that it is important for the gas flow to not directly impinge on the sensor surface since a direct impingement on the sensor surface with the reducing gas flow will likely alter the direct relationship of surface electrons to the conductivity of the sensor.

As previously mentioned, sensor surface is equivalent to a "bio-mass", breathing in oxygen and exhaling oxygen in the form of $SO_2$ and $H_2O$ when exposed to $H_2S$. Gas flows in through an inlet and flows out through the outlet (the other NPT threaded fitting mount) which is diametrically opposite the inlet so that the gas flow does not directly impinge on the surface of the sensor.

Figure 6:
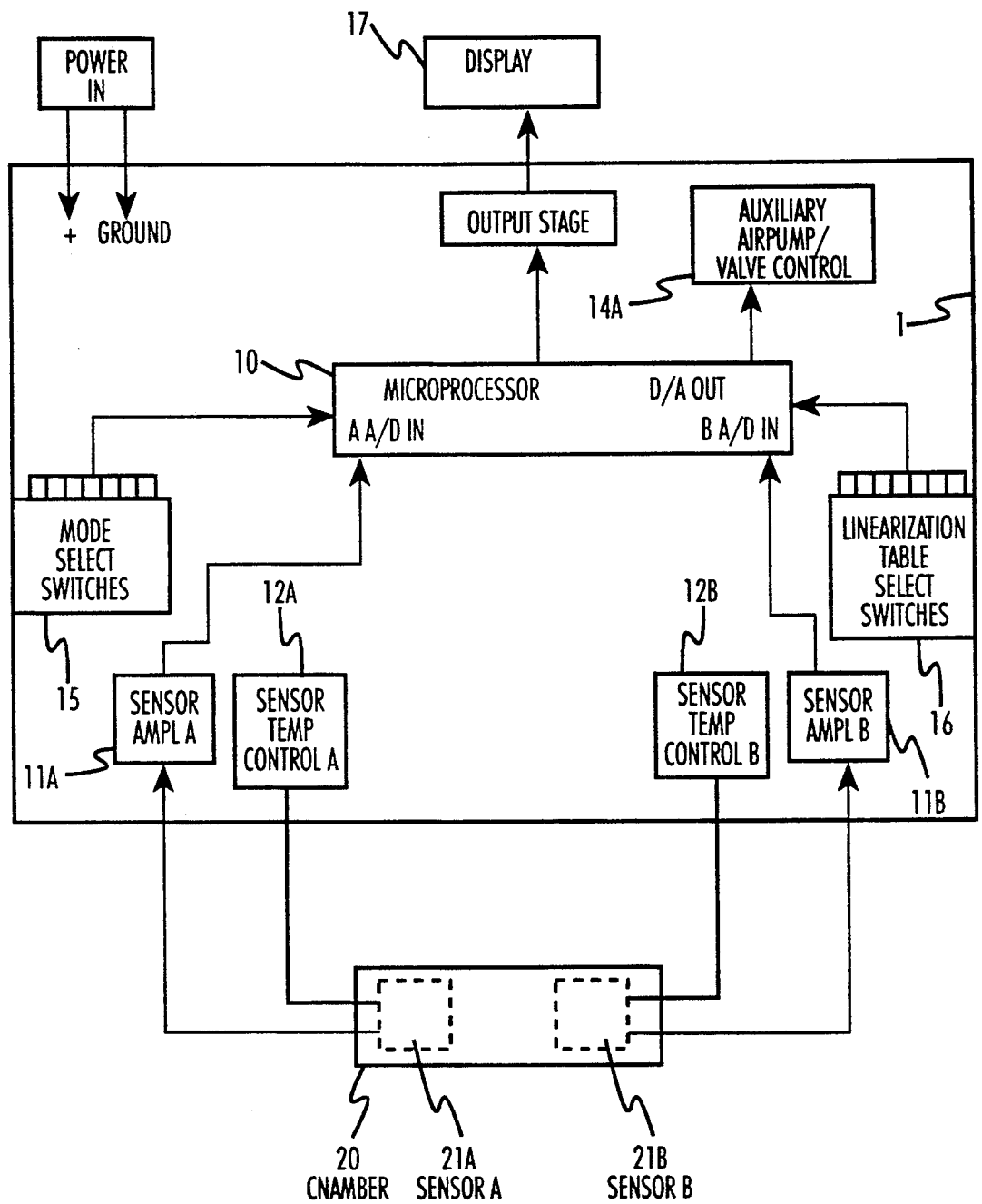
FIG. 6 is a second embodiment of the present invention which uses a single chamber with at least two metal oxide semiconductor sensors.

In the second embodiment of FIG. 6, as previously indicated, the same reference numerals as used in the first embodiment are used to identify the same elements. The second embodiment, as contemplated in FIG. 6, is for monitoring an ambient environment, such as air, for the presence of reducing gas, such as for monitoring gas leaks in industrial plants. The embodiment in FIG. 6 contemplates two sensors (21A, 21B) housed inside a single chamber (20). However, it is to be noted that the present invention is not limited to two sensors, as many more sensors could have been equally contemplated.

The second embodiment does not require any of the plumbing and the associated controls contemplated in the first embodiment. In this respect, by providing at least two sensors in the chamber, individual "stand alone" single point systems can be contemplated.

By simply having at least two metal oxides sensors in a single chamber and switching each of the sensors "on" and "off" alternatively, a similar effect as that of the first embodiment can be contemplated. Specifically, by shutting off the sensor (turning of the heating element in the sensor) the temperature of the metal oxide semiconductor can be cooled to about the ambient temperature. This causes the metal oxide semiconductor to replenish the depleted oxygen even though small level of the reducing gas can be present. At the room temperature, reducing gas in the air has no substantial effect on the sensor and oxidation may take place.

Figure 7:
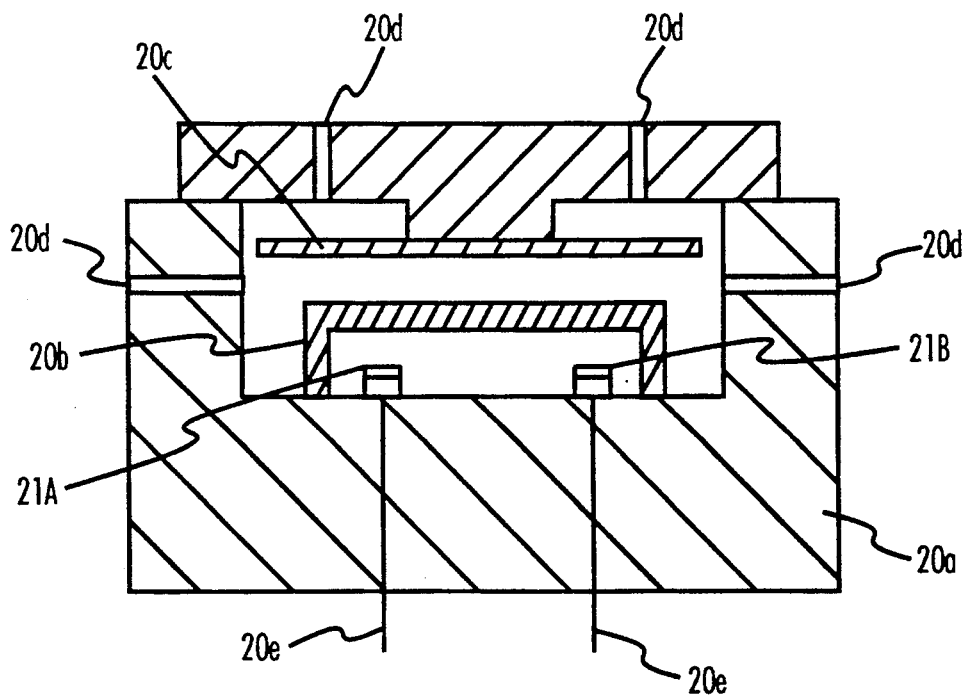
FIG. 7 is a single chamber for housing the metal oxide semiconductor sensors of the second embodiment.

FIG. 7 shows the details of a housing of the sensors of the second embodiment. In order to prevent the sensors, which are heated, from igniting flammable or explosive gases present in the environment and to prevent propagating of ignited gases, the housing which encloses the sensors should preferably meet the standard set forth by International Standard Association (ISA) and Canadian Standard Association (CSA) for ignition propagating containers. The housing per se does not form part of the present invention, as present invention contemplates use of a known housing commercially available or custom made from the standard set forth by ISA and CSA.

FIG. 7 illustrates a graphical representation of the housing which comprises a housing body (20a) positioned with a pair of sensors (21A, 21B) mounted on the surface thereof. A porous cup (20b), preferably of "316" stainless steel sintered material, shrouds over the sensors. The preferred sintered cup is porous to permit gas and air to permeate through the walls of the cup, but prevents ignited gas from propagating therethrough. Preferably, the nominal porosity of the cup should be around 20 microns. Further precautionary measures should preferably be used such as a baffle disc (20c) to cover the cup to further prevent propagation of gas ignited within the housing. The housing body (20a) and the baffle (20c) should have openings (20d) to permit gas and air to freely pass through. Wirings (20e) from the sensors are passed through the housing body (20a) for connection to the microprocessor which can be remotely located or connected directly to the housing body.

An example of the operation of the present device sampling natural gas for determining the content of $H_2S$ follows below:

The Operation of the First Embodiment

Gas and air pass through the gas lines (31) and exhausted to the outside via the exhausts after being passed through the chambers. Care must be taken during any installation or operation so that gas is not exposed to any form of heat or spark which might ignite it or cause an explosion. Furthermore, the exhausts should preferably have at least ⅛ inch inside diameter to prevent excessive back pressure at the chambers.

In the normal operation mode, only one sensor in the chambers at a time is active to read the hydrogen sulfide content. While one sensor is exposed to gas to measure the $H_2S$ content, the other sensor is shut off and is exposed to ambient air. After 15 minutes, the microprcessor sends a signal to the solenoid valve that controls the gas/air input of the other sensor that is exposed to the ambient air so that the gas flow is enabled and the air flow to the respective chamber disabled, and turns on the other sensor. For 5 minutes, both sensors receive gas and the microprocessor may turn off the air pump if desired. However, during this time, still only the one sensor takes the reading of the $H_2S$ content, the total sampling time being 20 minutes and the total air time being 15 minutes.

The sensor replenished with $O_2$ in air requires a finite time to reach its maximum output. To reach an optimum output, the other sensor, which was fed with air, is exposed to the gas for five minutes to normalize the sensor so that at the end of the five minute period, the sensor is at the optimum condition for reading the content of the reducing gas, the response period for reading becoming immediate.

After the 5 minute duration lapses, the roles of the sensors are reversed. The microprocessor activates the other sensor for reading and turns off the one sensor, and turns on the air pump if previously turned off. The microprocessor sends a signal to the solenoid valve that controls the gas/air input of the one sensor so that the ambient air flow to the respective chamber is enabled and the gas flow disabled for next 15 minutes. The other sensor now measures the hydrogen sulfide gas content during this period and additionally for the next 5 minutes. The air flow to the chamber with the one sensor purges any gas residue and replenishes the sensor with $O_2$. This cycle is endlessly repeated until either shut off or switched to a different mode.

While the operation of the first embodiment for detecting $H_2S$ gas has been contemplated with 20 minute for the gas time period, however, the time period could range from 15 to 25 minutes. By rhythmatically cycling gas/air at the frequency of 15 to 25 minute intervals, optimum response speed, consistency and accuracy of the sensor can be contemplated.

By rhythmatically cycling gas/air, coupled with the precision and consistency of the response speed of the sensor, the sensor is capable of reading high concentrations of $H_2S$ without being disabled or suffering from calibration shift. The sensors contemplated for use in the present device is preferably MEGASENSOR sold by Willis Technologies International.

When sampling gas containing a relatively high concentration of reducing gas, for example in the range above 1000 ppm for $H_2S$, in the normal 20 minute sampling period, $O_2$ may be depleted prior to the end of the 20 minute sampling period, which produces erroneous readings. To solve this problem, the present invention contemplates injecting air into the gas stream. This is achieved by using either an air pump or a solenoid valve connected to the gas line (31). When the solenoid valve is used, air can be introduced into the gas stream by venturi effect. Only a relatively small quantity of air need be introduced into the gas stream. Thus, a relatively small opening in the gas line is sufficient to introduce small quantities of air.

The Operation of the Second Embodiment

In the normal operation mode, the chamber (20) containing a pair of the metal oxide semiconductor sensors is placed in the environment containing $H_2S$, a reducing gas. The operation of the second embodiment is substantially similar as the first embodiment.

First, the microprocessor turns on only one of the two sensors for sampling for an interval between 15 and 25 minutes, while the other sensor remains idle. At the end of this interval, the microprocessor turns on the other sensor. As in the first embodiment, the other sensor remains inactive for sampling. After an interval of 5 minutes, the microprocessor turns off the one sensor and activates the other sensor for sampling for an interval between 15 and 25 minutes. This cycle is continuously repeated. During the time the sensors are turned off, the depleted oxygen is replenished, as previously discussed. To reach an optimum output, the other sensor is turned on to normalize with the reducing gas so that at the end of the five minute period, the sensor is at the optimum condition for reading the content of the reducing gas, the response period for reading becoming immediate.

In the first and second embodiments, while it is not necessary, different mode selection of the operation is contemplated. The mode select switches (15) can be adopted for changing the cycle time. The above described mode, the normal mode, can be one mode. Another mode can be a cycle time mode which is basically identical to the normal mode, but the cycle times are reduced to seconds. For example, instead of on and off period of 20 minutes, it can be contemplated to 20 second. Instead of normalizing state of 5 minutes, it can be contemplated to 5 seconds.

If the cycle time mode is utilized, the auxiliary air pump or solenoid valve (22a) is not required since the time duration of 20 seconds is not long enough to cause a total $O_2$ deprivation.

Another mode contemplated is in which the gas/air time can be manually programmed via push-buttons (not shown).

Another mode contemplated is a manual mode. In this mode, the gas chambers do not change state. That is, they stay "frozen" in their present operation state and do not cycle automatically. Rather, each of the solenoid valves can be manually controlled, for example with air and gas pushbutton switches (not shown). In this mode, the gas chambers can be used to apply air or gas to both chambers simultaneously to check the flow. Many other modes of operation can be contemplated from the present disclosure without departing from scope of the present invention. For example, one skilled in the art could contemplate providing an operation mode where both chambers simultaneously sample gas and automatically purge both chambers at a predetermined interval.

Moreover, the pair of sensors can be of different type. For example, one sensor can be of the type catered for reading a relatively high concentration level of reducing gas while the other sensor can be of the type catered for reading a relatively low concentration level of reducing gas since each of the sensor has a separate, independent channel in the microprocessor, which can be calibrated for an optimum sampling suited to the particular application. This may be contemplated by using separate linearization settings (16) for calibrating and testing of the sensors.

The foregoing description and drawings are merely illustrative of the principles of the present invention. It is to be noted that the present invention is not to be limited only to the exact configuration and construction and the operations as illustrated and described herein. For example, while the gas/air time was contemplated between 15 to 25 minutes and 20 seconds for $H_2S$, other gas/air time could be contemplated for optimal gas/air time could be contemplated for use with various reducing gases. Accordingly, all expedient modifications which may be made within the scope and spirit of the present invention is to be contemplated as being disclosed herein.

I claim:

1. A device for detecting and measuring gas content of the type which depletes oxygen component from a semiconductor type of gas sensor upon exposure thereto, comprising:

a first chamber housing a first gas sensor of said semiconductor type, said first chamber having a first input means for inputting gas to be sampled or air, and a first output means for exhausting the inputted gas or air;

a second chamber housing a second gas sensor of said semiconductor type, said second chamber having a second input means for inputting gas to be sampled or air, and a second output means for exhausting the inputted gas or air;

means operatively connected to said first and second input means for inputting air;

means operatively connected to said first and second input means for inputting gas;

a flow control means connected between said first and second chambers, said air inputting means and said gas inputting means for controlling the flow of gas and air to said first and second chamber, wherein said flow control means permits either gas or air to flow through said first chamber and permits either gas or air to flow through said second chamber; and a microprocessor means connected to said first and second sensors for controlling said sensors and for converting output signals from said first and second sensors to a readable format indicative of the content of the oxygen depleting gas, and connected to said flow control means for controlling said flow control means to permit either gas or air to said first and second chambers.

2. The device according to claim 1, wherein said microprocessor means controls said flow control means to alternatively permit air to flow through one chamber and permit gas to flow through the other chamber for a first predetermined period, and wherein said microprocessor alternatively turns off the sensor in said one chamber for said first predetermined period and turns on the sensor in said other chamber to sample gas for said first predetermined period.

3. The device according to claim 2, wherein said microprocessor means controls said flow means to permit gas to flow through said one chamber for a second predetermined period after said first predetermined period, and wherein said microprocessor turns on said sensor in said one chamber.

4. The device according to claim 3, wherein said microprocessor means controls said flow means to permit air to flow through said other chamber and turns off said sensor in said other chamber for said first predetermined period after said second predetermined period, and wherein said microprocessor means activates said sensor in said one sensor for sampling for said first predetermined period after said second predetermined period.

5. The device according to claim 2, wherein said gas is $H_2S$.

6. The device according to claim 1, wherein said flow control means is a pair of solenoid valves, one connected between said gas inputting means and one of said chambers, and the other connected between said air inputting means and the other of said chambers.

7. The device according to claim 6, further comprising a flow meter connected between each of the chambers and the respective solenoid valve.

8. The device according to claim 6, further comprising a flow meter connected between each of said solenoid valves and said air inputting means.

9. The device according to claim 6, further comprising an auxiliary air inputting means connected between said gas inputting means and said chambers to inject or introduce air into the gas flow.

10. A device for detecting and measuring gas content of the type which depletes oxygen component from a semiconductor type of gas sensor upon exposure thereto, comprising:

a first chamber having a first gas sensor of said semiconductor type which outputs a signal in response to exposure to the gas which depletes oxygen from said first sensor;

a first input means for inputting gas or air into said first chamber;

a first output means for exhausting the inputted gas or air out of said first chamber;

a second chamber having a second gas sensor of said semiconductor type which outputs a signal in response to exposure to said oxygen depleting gas;

a second input means for inputting gas or air into said second chamber;

a second output means for exhausting the inputted gas or air out of said second chamber;

means for inputting air source to said first and second chamber via said first and second input means;

means for inputting gas source to said first and second chamber via said first and second input means;

a first flow control means having a first flow output means and a first pair of flow input means, said first flow output means being connected to said first input means of said first chamber; one of said first pair of flow input means connected to said air source inputting means; and the other of said first pair of flow input means connected to said gas source inputting means, wherein said first flow control means permits either gas or air to flow through said first chamber;

a second flow control means having a second flow output means and a second pair of flow input means, said second flow output means being connected to said second input means of said second chamber; one of said second pair of flow input means connected to said air source means; and said other of said second pair of flow input means connected to said gas source inputting means, wherein said second flow control means permits either gas or air to flow through said second chamber;

a control means connected to said first and second sensors for controlling said first and second sensors and for converting output signals from said first and second sensors to a readable format indicative of the content of said oxygen depleting gas, connected to said first flow control means, said second flow control means and connected to said air source inputting means for controlling air and gas flow through said first and second chambers, wherein said control means permits said first flow control means to flow gas through said first chamber while permitting said second flow control means to flow air through said second chamber for a first predetermined duration; and after said first predetermined duration, said microprocessor means permits said second flow control means to flow gas through said second chamber for a second predetermined duration while said first chamber remains flowing with gas; after said second predetermined duration, said microprocessor permits said first flow control means to flow air through said first chamber while said second chamber remains flowing with gas for said first predetermined duration; and after said first predetermined duration, said microprocessor permits said first flow control means to flow gas through said first chamber while said second chamber remains flowing with gas for said second predetermined period; and repeatedly alternating the flow of gas and air to said first and second chambers for said first predetermined duration and gas-up for said second predetermined duration; and a display for displaying the oxygen depleting gas content from either said first and second sensors.

11. The device according to claim 10, wherein said microprocessor means turns off each of said first and second sensors during the period in which said each of said sensors is exposed to air and turns on each of said first and second sensors during the period in which said each of said sensors is exposed to gas for sampling for said first predetermined duration, and wherein said each of said first and second sensors which was sampling for said first predetermined duration remains active for sampling after said first predetermined duration for said second predetermined duration, while each of said first and second sensors that was fed with air for said first predetermined duration is turned on after said first predetermined duration for said second predetermined duration, but remains inactive for sampling until after said second predetermined duration.

12. The device according to claim 11, wherein said gas is $H_2S$.

13. The device according to claim 10, further comprising an auxiliary air inputting means connected upstream of said first and second flow control means and downstream of said gas inputting means.

14. A method for detecting and measuring gas content of the type which depletes oxygen component from a semiconductor type of gas sensor in gas to be sampled, lowering electrical resistance across the semiconductor gas sensor upon exposure thereto, comprising the steps of:
  a) exposing a first gas detecting sensor of said semiconductor type to gas to be sampled to detect the oxygen depleting gas content continuously for a first predetermined duration and for another second predetermined duration;
  b) exposing a second gas detecting sensor of said semiconductor type to ambient air during said first predetermined duration in step a) and exposing said second gas detecting sensor to said gas during said first and second predetermined duration in step a);
  c) reading the electrical resistance across said first sensor to determine the content of said oxygen depleting gas during said first and second predetermined durations in step a);
  d) maintaining exposure of said second sensor to said gas for another first and second predetermined durations;
  e) reading the electrical resistance across said second sensor to determine the content of said oxygen depleting gas during said first and second predetermined durations in step d);
  f) exposing said first sensor to ambient air to remove any gas residue and to replenish said first sensor with oxygen depleted therefrom during said first predetermined duration in step d) and exposing said first sensor to said gas during said second predetermined duration in step d);
  g) repeating the steps a)-f).

15. The method according to claim 14, wherein said gas is $H_2S$.

16. The method according to claim 14, wherein said first sensor is housed in a first chamber and said second chamber is housed in a second chamber, said first and second chamber being isolated from each other.

17. A device for monitoring reducing gas in gas containing oxygen, comprising:
  a chamber having at least a pair of gas sensors of a semiconductor type which outputs a signal in response to exposure to reducing gas which depletes oxygen from said sensors;
  means in said chamber for permitting said gas containing oxygen to permeate through said gas chamber to expose said gas sensors thereto;
  a control means having a corresponding number of discrete, independent channels for connecting the outputs of said at least two sensors, converting the output signals from said first and second sensors to a readable format indicative of the content of said reducing gas and means for turning on and off said sensors,
  wherein said control means provides means for turning on and activating one of said at least two sensors for sampling the content of reducing gas while said other of said at least two sensors is turned off, for a first predetermined duration; means for turning on said other of said at least two sensors while said one sensor remains active for sampling after said first predetermined duration, for a second predetermined duration; means for activating said other sensor for sampling and turning off said one sensor after said second predetermined duration, for said first predetermined duration; and means for repeating said turning on and off, alternatively between said at least two sensors.

18. The device according to claim 17, wherein said oxygen containing gas is air and said reducing gas is $H_2S$.

19. A method for monitoring reducing gas in gas containing oxygen, comprising the steps of:
  a) providing at least a pair of sensors in a chamber which is porous as to permeate said oxygen containing gas and reducing gas;
  b) turning on one of said sensors continuously for a first predetermined duration and for a second predetermined duration;
  c) turning off the other of said sensors during said first predetermined duration and turning on said other of said sensors during said second predetermined duration in step b);
  d) reading signals output from said one sensor during said first and second predetermined durations in step b) to determine the content of said oxygen depleting gas;
  e) maintaining said other sensor on for another said first and second predetermined durations;
  f) reading signals output from said other sensor during said first and second predetermine durations in step e) to determine the content of said oxygen depleting gas;
  g) turning off said one sensor for said first predetermined duration and turning on said one sensor for said second predetermined duration, respectively during said first and second predetermined durations in step e)
  h) repeating the steps b)-g).

20. The device according to claim 19, wherein said oxygen containing gas is air and said reducing gas is $H_2S$.

21. A method for detecting and measuring gas content of the type which depletes oxygen component from a semiconductor type of gas sensor in gas to be sampled, lowering electrical resistance across the semiconductor gas sensor upon exposure thereto, comprising the steps of:

a) providing first and second chambers, each containing a gas sensor of said semiconductor type;
b) flowing gas to be sampled through said first chamber;
c) flowing ambient air to said second chamber while said first chamber is flowing with gas;
d) reading signals output from the gas sensor in said first chamber to determine the content of said oxygen depleting gas during steps b) and c);
e) stopping the flow of ambient air through said second chamber and flowing the gas to be sampled therethrough instead;
f) reading signals output from the sensor in said second chamber to determine the content of said oxygen depleting gas during step e);
g) stopping the flow of the gas to be sampled to said second chamber and flowing instead with ambient air to remove any gas residue remaining therein and to replenish the oxygen depleted from the sensor in said first chamber during step e);
h) repeating the steps b)-g).

22. The method according to claim 21, wherein said gas is $H_2S$.

* * * * *